(12) United States Patent
Haider et al.

(10) Patent No.: US 6,840,921 B1
(45) Date of Patent: Jan. 11, 2005

(54) APPARATUS AND METHODS FOR SIMULTANEOUSLY ADMINISTERING TWO OR MORE MEDICATIONS TO A PATIENT

(75) Inventors: Timothy D. Haider, 17572 Bonner Dr., Santa Ana, CA (US) 92705; Monica R. Haider, 17572 Bonner Dr., Santa Ana, CA (US) 92705; Carl TenBrink, Huntington Beach, CA (US); David Bain, Huntington Beach, CA (US)

(73) Assignees: Timothy D. Haider, Santa Ana, CA (US); Monica R. Haider, Santa Ana, CA (US)

( * ) Notice: Subject to any disclaimer, the term of this patent is extended or adjusted under 35 U.S.C. 154(b) by 27 days.

(21) Appl. No.: 10/340,415

(22) Filed: Jan. 10, 2003

Related U.S. Application Data

(60) Provisional application No. 60/391,475, filed on Jun. 25, 2002, and provisional application No. 60/347,639, filed on Jan. 11, 2002.

(51) Int. Cl.[7] .............................. A61M 5/00; A61M 5/32
(52) U.S. Cl. ....................................... 604/191; 604/198
(58) Field of Search ........................... 604/82, 191, 197, 604/198, 192; 222/135, 134, 137, 325, 327

(56) References Cited

U.S. PATENT DOCUMENTS

| | | |
|---|---|---|
| 3,467,096 A | 9/1969 | Horn ........................... 128/218 |
| 3,552,394 A | 1/1971 | Horn ........................... 128/218 |
| D246,187 S | 10/1977 | DeArment .................... D24/14 |
| 4,109,653 A | 8/1978 | Kozam et al. ............... 128/218 |
| 4,150,669 A | 4/1979 | Latorre ......................... 128/79 |
| 4,226,235 A | * 10/1980 | Sarnoff et al. .............. 604/136 |
| 4,260,077 A | 4/1981 | Schroeder .................... 222/137 |
| 4,367,737 A | 1/1983 | Kozam et al. ............... 128/215 |
| 4,381,778 A | 5/1983 | Kozam et al. ............... 604/191 |
| 4,610,666 A | 9/1986 | Pizzino ........................ 604/191 |
| 4,979,942 A | 12/1990 | Wolf et al. .................... 604/83 |
| 5,116,315 A | 5/1992 | Capozzi et al. ............... 604/82 |
| 5,290,259 A | 3/1994 | Fischer ........................ 604/218 |
| 5,314,412 A | 5/1994 | Rex .............................. 604/191 |
| 5,725,499 A | 3/1998 | Silverstein et al. ........... 604/82 |
| 5,846,225 A | * 12/1998 | Rosengart et al. .......... 604/115 |
| 6,312,412 B1 | 11/2001 | Saied et al. ................. 604/191 |

* cited by examiner

*Primary Examiner*—Michael J. Hayes
(74) *Attorney, Agent, or Firm*—Stout, Uxa, Buyan & Mullins, LLP; Greg S. Hollrigel

(57) ABSTRACT

A medical injection apparatus for simultaneously administering two or more medications to a patient includes a housing that is structured to hold two or more syringes in a substantially fixed relationship so that the distal ends of the syringe needles are spaced apart from each other. The housing may be structured for reuse, or may be disposable. The housing may include two portions that are identically structured, each portion defining half of the housing. The housing may also include a syringe sleeve that is deployable from a first position in which the needles of the syringes are exposed to a second position in which the needles of the syringes are not exposed.

12 Claims, 6 Drawing Sheets

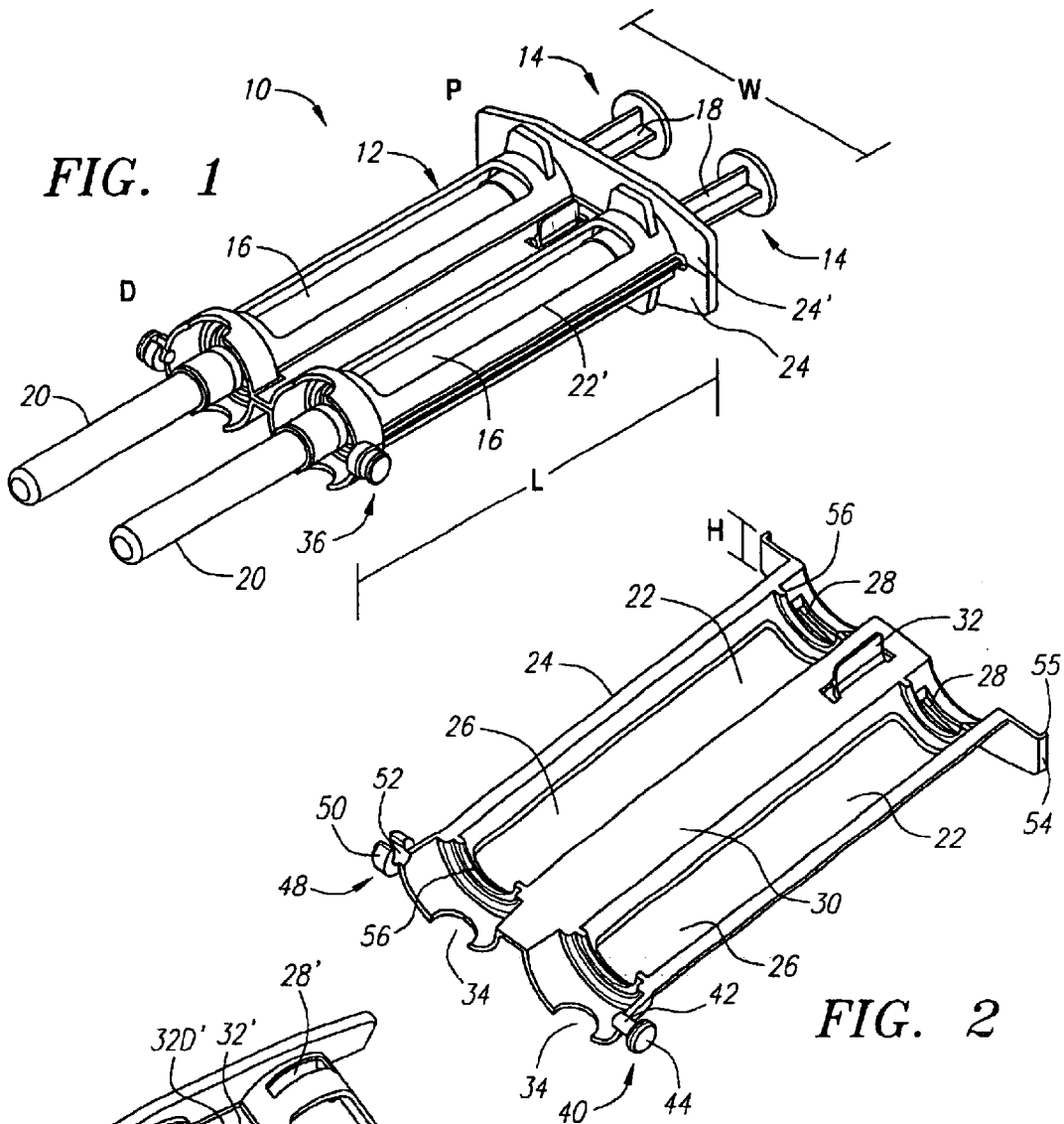
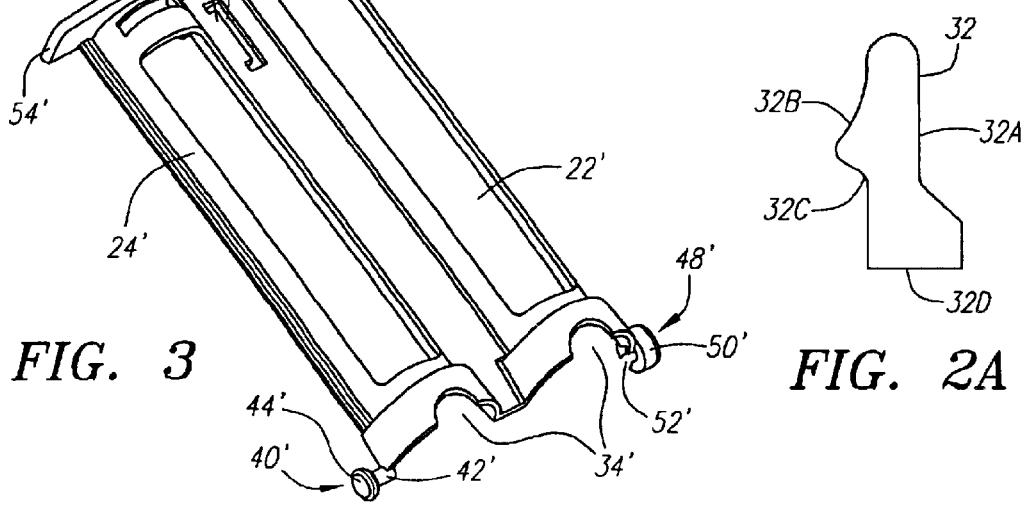

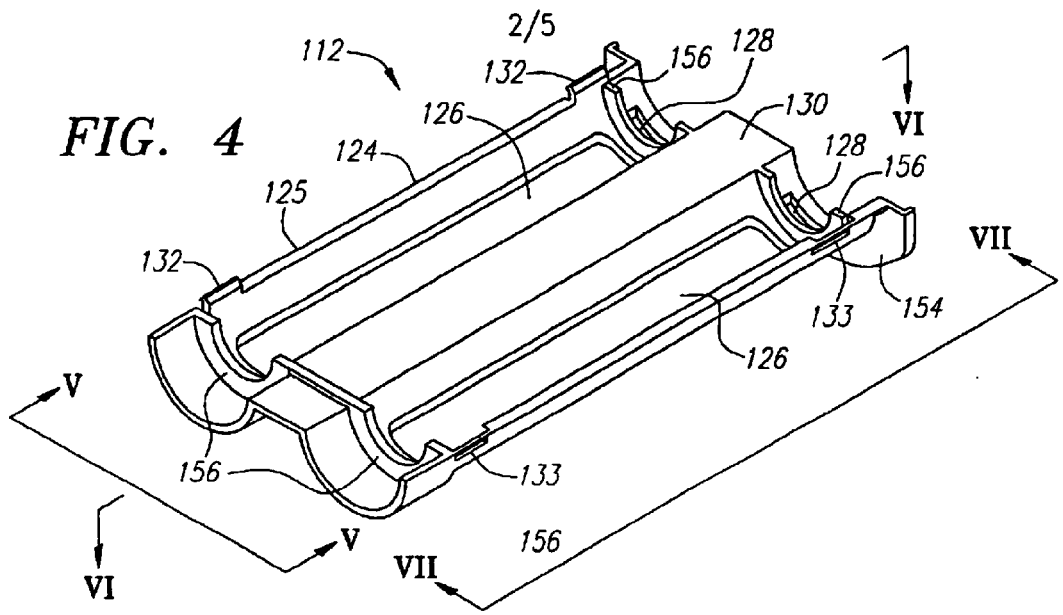
FIG. 4
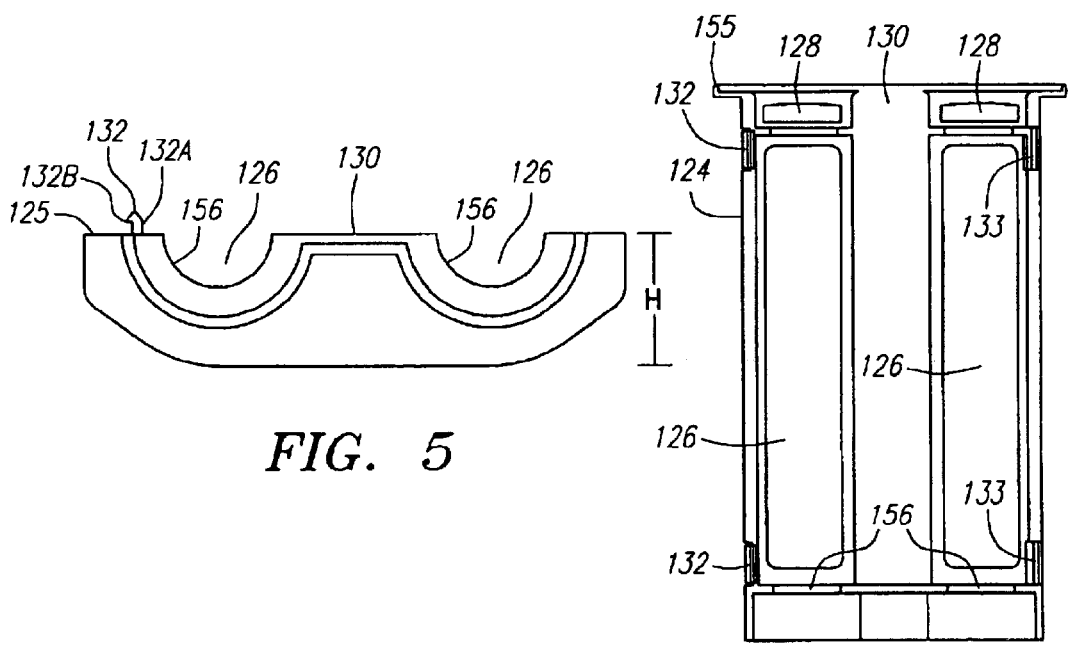
FIG. 5
FIG. 6
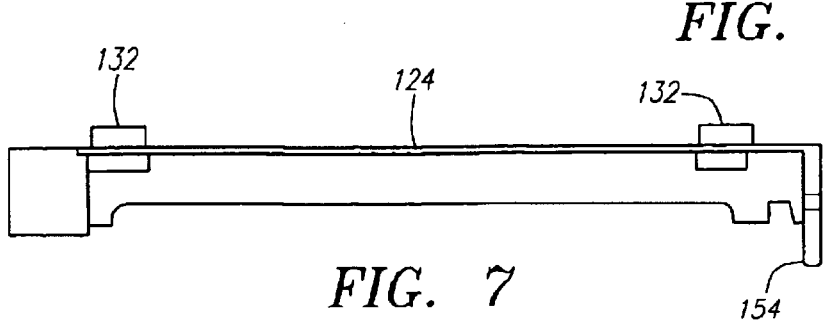
FIG. 7

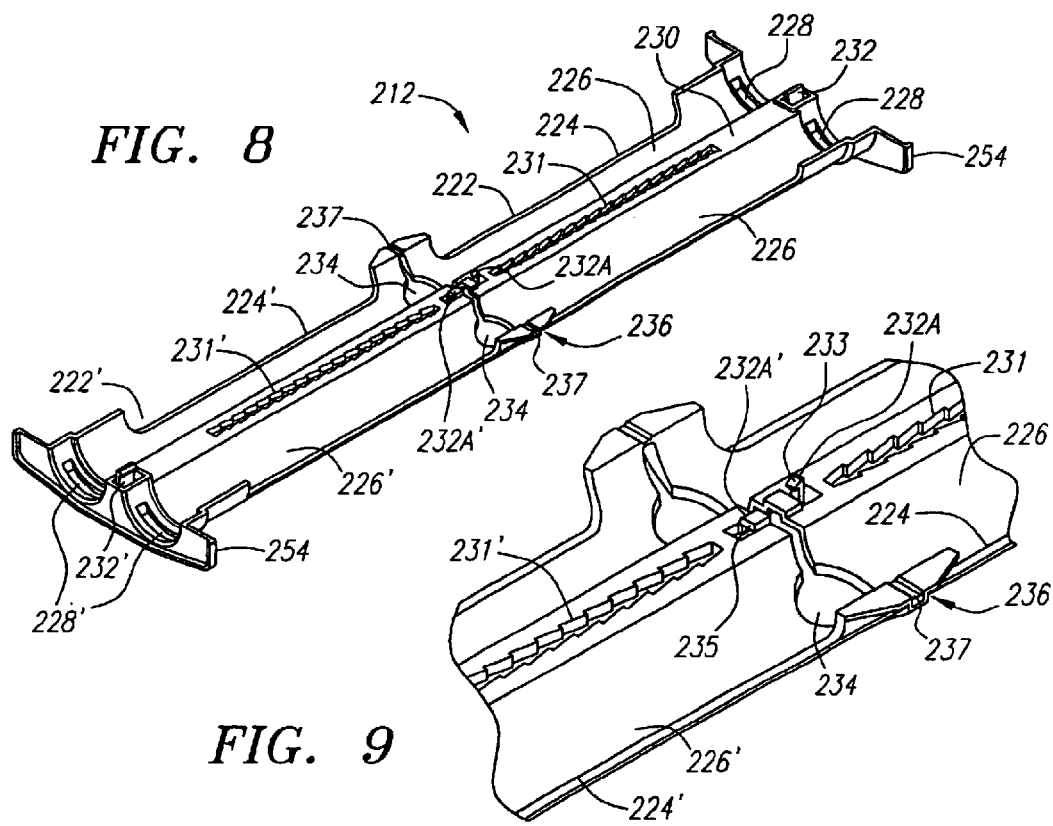
FIG. 8
FIG. 9
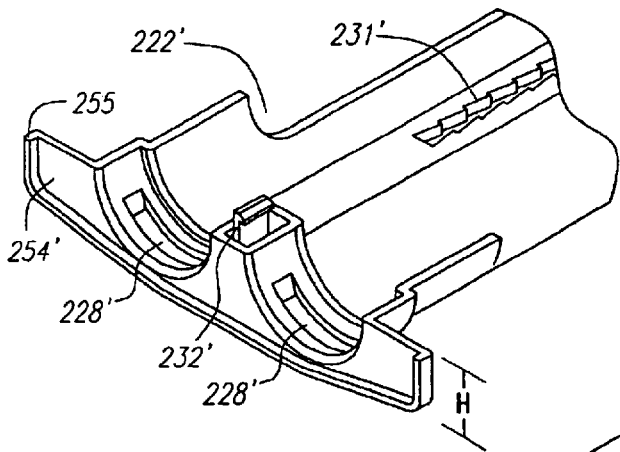
FIG. 10
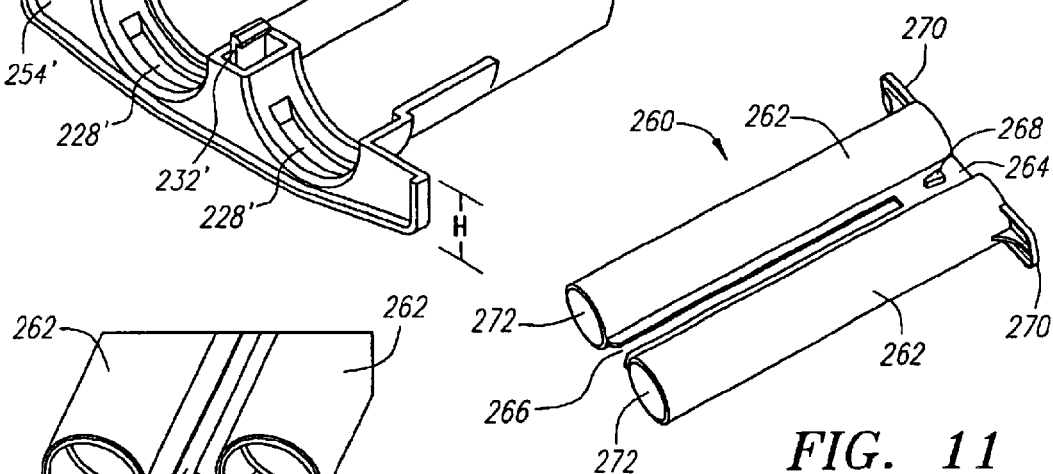
FIG. 11
FIG. 12

FIG. 13
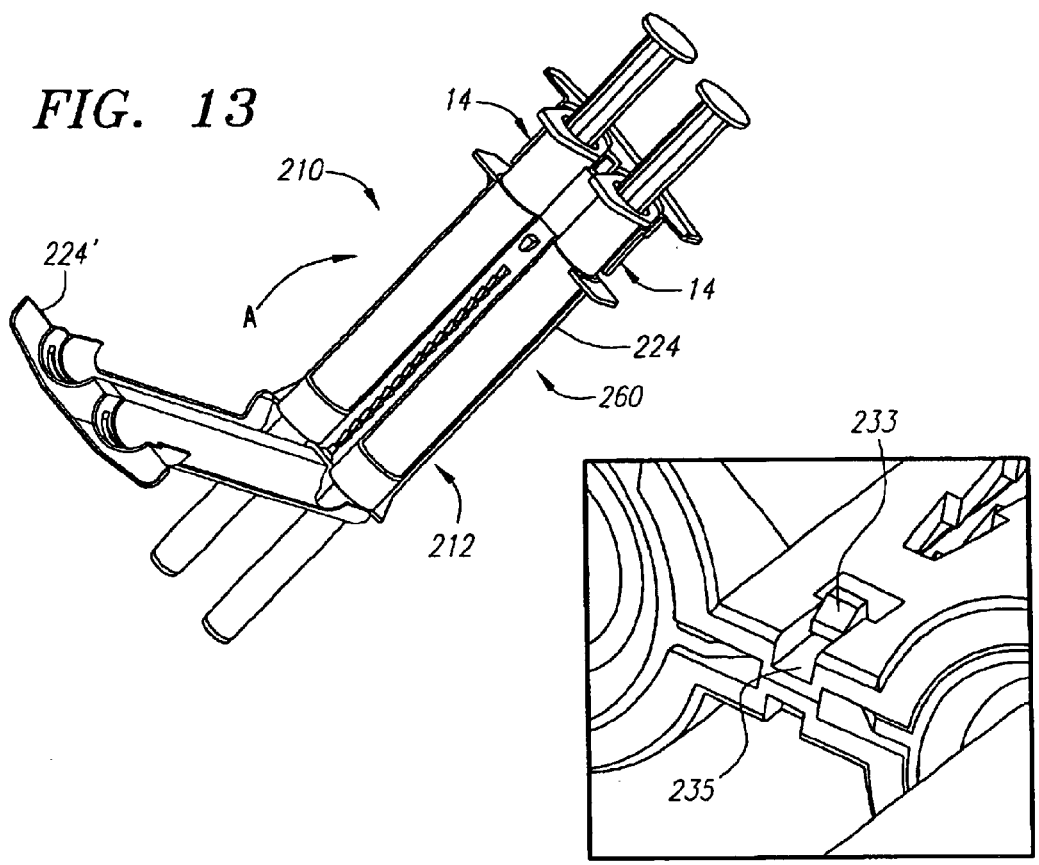
FIG. 14
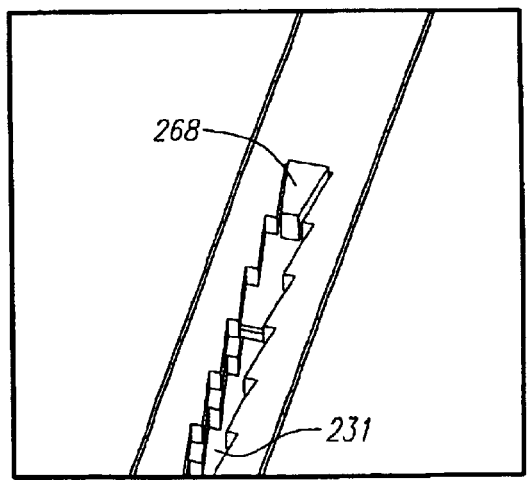
FIG. 15
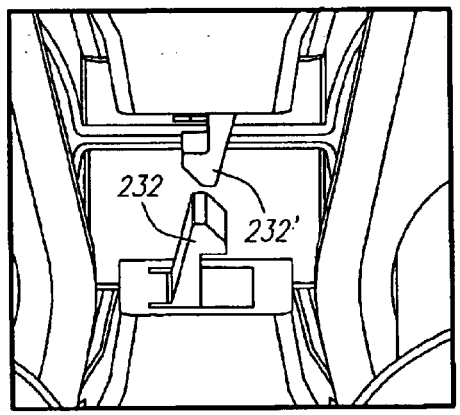
FIG. 16

APPARATUS AND METHODS FOR SIMULTANEOUSLY ADMINISTERING TWO OR MORE MEDICATIONS TO A PATIENT

CROSS-REFERENCE TO RELATED APPLICATIONS

This application claims the benefit of U.S. Provisional Application No. 60/347,639, filed Jan. 11, 2002 and U.S. Provisional Application No. 60/391,475, filed Jun. 25, 2002, the entire contents of which are hereby incorporated by reference.

FIELD OF THE INVENTION

This invention relates to medical devices and methods of using same. More particularly, the invention relates to medical injection apparatus and methods for simultaneously administering two or more medications to a patient at the same time.

BACKGROUND

Nearly all syringes used today have been developed to provide individual injections of a medication or medications to a human or animal patient using a single syringe/needle, meaning that one syringe (and one needle) are used to administer the medication. If two medications are needed for a patient, then two syringes (and two needles) are used with each medication and are administered at separate times and at separate parts of the patient's body. The use of multiple syringes and injections not only prolongs the injection process, but it also increases the exposure to dangerous needle "sticks" on the part of the person who is administering the injections. Similarly, these devices do not adequately address the increased trauma a patient experiences with multiple injections.

Attempts have been made to provide devices that hold more than one syringe so that medications contained in each syringe are administered to a patient, such as those disclosed in U.S. Pat. Nos. 3,467,096; 3,552,394; 4,150,669; 6,312,412; and D246,187. However, these devices are relatively complicated, are expensive to manufacture, and do not provide safety mechanisms to reduce potential inadvertent injuries from the syringe needles.

Thus, there remains an unmet need in the art for apparatus and methods that reduce the amount of time to deliver multiple injections, reduces the trauma experienced by a patient, and/or increases healthcare safety. There also remains a need for such devices that are relatively simple to manufacture.

SUMMARY

A medical injection apparatus for administering two or more medications to a patient, comprises a housing that includes at least two recesses along the length of the housing and dimensioned to maintain a corresponding number of syringes in a substantially fixed relationship to each other, and a syringe sleeve located around the syringes and being moveable from a first position in which the hypodermic needles of the syringes are exposed for administration of a medication to a patient, to a second position in which the hypodermic needles are not exposed to prevent inadvertent injury from the needles.

The housing of the foregoing apparatus may include two complementary portions that matingly engage to define two or more cylindrical recesses. In certain embodiments, the first portion and the second portion are identically structured. The housing may also include a hinge assembly that defines a pivot axis about which the first portion and/or second portion pivots. The pivot axis is oriented parallel to the width of the housing. The distal ends of the first portion and second portion may also include a cutout sized to accommodate a distal end of each syringe as the first portion or second portion pivots about the pivot axis. The hinge assembly may be a flexible web, a pin and clamp assembly, a ball and socket assembly, or a pin and hole assembly. One or more locking devices may be provided on the first and second portions to maintain a secure engagement of the two portions of the housing. In certain embodiments, the locking devices are flexible members that include a lip to engage with a similar structure on the other portion of the housing. The syringe sleeve of the apparatus may be located around the housing and includes one or more locking devices that engage with a locking device provided on the housing. In other embodiments, the syringe sleeve may be located in the housing around the syringes. In still further embodiments, the syringe sleeve may include a plurality of syringe containers coupled together by a connecting portion, and including a rib that engages with a track provided on the housing.

A medical injection apparatus for simultaneously administering two or more medications to a patient also comprises a housing having a plurality of recesses to hold a plurality of syringes in a substantially fixed relationship, and including two portions that are identically structured, each portion defining half of the housing.

The foregoing apparatus includes one or more locking devices located on each of the two portions, and being positioned so that the locking devices engage with each other. The housing may include a hinge assembly that defines a pivot axis parallel to the width of the housing. The hinge assembly may include a flexible web of material, or may include a pin and clamp assembly, a ball and socket assembly, or a pin and hole assembly. In certain embodiments, the apparatus includes a syringe sleeve that is deployable from a first position in which the syringe needles are exposed, to a second position in which the syringe needles are not exposed. The locking devices of the foregoing apparatus may be structured to prevent the housing from being manually disassembled after the medications are administered to a patient.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description.

BRIEF DESCRIPTION OF THE FIGURES

FIG. 1 provides a perspective view of a medical injection apparatus for simultaneously injecting two medications to a patient.

FIG. 2 provides a perspective view of a first portion of a housing of the medical injection apparatus of FIG. 1.

FIG. 2A provides a plan view of the locking device of FIG. 2.

FIG. 3 provides a perspective view of a second portion of a housing of the medical injection apparatus of FIG. 1.

FIG. 4 provides a perspective view of a first portion of a housing of a medical injection apparatus for simultaneously administering two medications to a patient.

FIG. 5 provides a plan view along line V—V of FIG. 4.

FIG. 6 provides a plan view along line VI—VI of FIG. 4.

FIG. 7 provides a plan view along line VII—VII of FIG. 4.

FIG. 8 provides a perspective view of a first portion and a second portion of a housing of a medical injection apparatus for simultaneously administering two medications to a patient.

FIG. 9 provides a magnified view of the hinge assembly of the housing of FIG. 8.

FIG. 10 provides a magnified view of a locking assembly of the housing of FIG. 8.

FIG. 11 provides a perspective view of a syringe sleeve for use with the housing of FIG. 8.

FIG. 12 provides a magnified view of the distal ends of the syringe sleeve of FIG. 11.

FIG. 13 provides a perspective view of a medical injection apparatus using the housing of FIG. 8.

FIG. 14 provides a magnified view of a locking assembly located near the hinge portion of the apparatus of FIG. 13 after the locks have been engaged.

FIG. 15 provides a magnified view of a locking assembly located near the proximal end of the apparatus of FIG. 13 just prior to engagement.

FIG. 16 provides a magnified view of a ratchet assembly of the apparatus of FIG. 13.

DETAILED DESCRIPTION

Figure 17A:
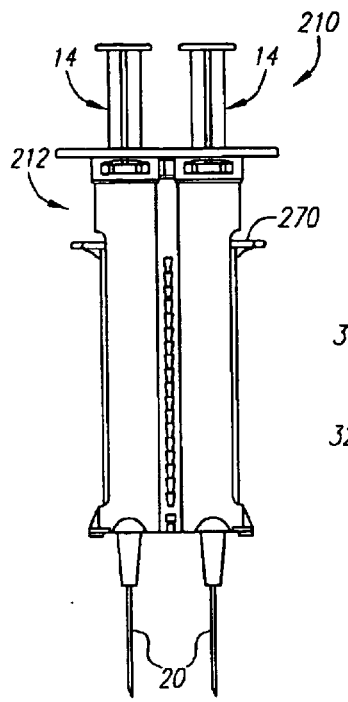
FIG. 17A provides a plan view of the medical injection apparatus of FIG. 13 with the syringe sleeve in a retracted position, and the hypodermic needles exposed.
Figure 18:
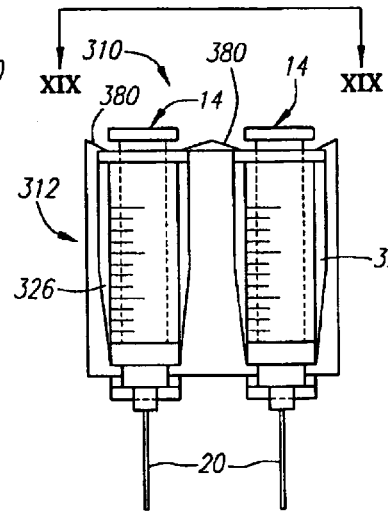
FIG. 18 provides a plan view of a medical injection apparatus for simultaneously administering two medications to a patient.

A medical injection apparatus for simultaneously administering two or more medications to a patient, as disclosed herein, includes a housing or holder that holds two or more syringes in a substantially fixed relationship so that when an injection is given to a human or animal patient, all of the hypodermic needles of the syringes penetrate the patient's skin at approximately the same time. As used herein, the phrase "simultaneously administered" refers to the administration of multiple substances contained in the syringes at nearly the same time, or in other words, administration of the substances during a single injection procedure. The housing is structured to hold a plurality of syringes of any size, and particularly, conventionally sized syringes, such as 1 mL, 3 mL, 5 mL, 10 mL, and 20 mL syringes. The housing can hold two or more syringes of the same size, or can hold syringes of different sizes. Although the illustrated embodiment of the apparatus is configured to hold two syringes, additional embodiments can hold more syringes as desired. Because it may be desirable to reduce mixing of separate medications when administering medications to a patient, the housing of the medical injection apparatus may be structured to keep the distal ends of the hypodermic needles spaced apart by at least one inch. However, when mixing of the medications is acceptable or desirable, the housing of the medical injection apparatus may be structured to keep the distal ends of the needles spaced apart by less than one inch. A medical injection apparatus, as disclosed herein, includes a housing, as described above, and a safety sleeve or syringe sleeve that can be deployed to cover the needles of the syringes to reduce accidental "sticking" by the needles. A medical injection apparatus, as disclosed herein, also includes a housing formed of two units or portions, each portion being identically structured to the other portion.

The components of the medical injection apparatus should be made of a material that is sufficiently strong to maintain a fixed positional relationship between the syringes held in the housing of the apparatus. The housing should also be structured to permit the contents contained in the syringe to be viewed (e.g. for volumetric determination). In certain embodiments, apertures may be provided in the housing. In other embodiments, the housing, and/or other components of the apparatus may be made of transparent or translucent material so that the contents in the syringes may be viewed. In still further embodiments, the housing, may include one or more viewing apertures, and be made of transparent or translucent materials. In one embodiment, the components of the medical injection apparatus are made of plastic, such as polypropylene. However, other materials, such as polycarbonate, may be used so long as they are sufficiently strong, and can be sterilized (e.g., autoclaved or irradiated) without degradation. To reduce manufacturing costs, the components of the medical injection apparatus are injection molded from plastic using conventional injection molding techniques. The housing of the medical injection apparatus may also be color coded to provide a coding scheme for the size of the syringes to be held in the housing or for cosmetic reasons.

Referring to the embodiments illustrated in the figures, FIGS. 1–3 illustrate a housing for a medical injection apparatus that is intended to be reused. In other words, the housing illustrated in FIGS. 1–3 is structured to temporarily, but securely, retain two or more syringes in a spaced apart, fixed relationship. After a plurality of injections are administered to a patient, at approximately the same time, the housing is structured to be manually opened to permit a user to remove the syringes contained therein, without damaging the housing or the components of the housing.

More specifically, FIG. 1 illustrates a medical injection apparatus 10 for administering two or more medications to a patient at the same time. Medical injection apparatus 10 comprises a housing or frame 12 and two or more syringes 14 held in a fixed relationship in holder 12. Each syringe 14 includes a barrel 16, a plunger 18, and a needle 20, which is shown as being capped in FIG. 1. Each syringe 14 is fixed in housing 12 so that the hypodermic needle 20 of each syringe 14 is spaced at least one inch apart from each other, and so that the distal tips of the needles are equally spaced from the distal ends of syringes 14. As indicated above, other embodiments may space the needles closer together or farther apart. Medical injection apparatus 10 includes a distal end D and a proximal end P, and has a length L extending from the distal end D to the proximal end P. As used herein, the distal end of medical injection apparatus, or the components of the apparatus refer to the portion of the device that is closest to the syringe needles when fully assembled. The proximal end is the end opposite the distal end. Housing 12 has a plurality of viewing apertures 22' (and 22 not shown) to permit the contents of the syringes to be viewed. These apertures also permit a user to manipulate and/or grip a sleeve disposed around one or more of the syringes placed in housing 12, as discussed herein. Housing 12 also includes a hinge assembly 36, as discussed herein.

As illustrated in FIG. 1, housing 12 includes a first portion 24 and a second portion 24'. In the illustrated embodiment, first portion 24 and second portion 24' are identically structured. For clarity, and due to their identical structural features, like parts of the first portion and the second portion are identified by like numbers, where the parts of the second portion are identified by an apostrophe. Details of first portion 24 of housing 12 of medical injection apparatus 10 are shown in FIG. 2. As illustrated in FIG. 2, first portion 24 is equal to half of housing 12. First portion 24 has a distal end and a proximal end, and has a plurality of recesses 26 extending along the length of first portion 24 from the distal end to the proximal end. Each recess 26 is illustrated with a syringe viewing aperture 22, as discussed herein. Recess 26 also includes a plurality of slots 28 located in proximity of proximal end of first portion 24. Slots 28 are dimensioned to receive a shoulder of syringes 14. In the illustrated embodiment, slots 28 have the same width as apertures 22. Because first portion 24 and second portion 24' are identically structured, recesses 26 each have a hemicylindrical cross-section. Each recess 26 is separated and connected by a connecting portion or bridge 30, which defines a substantially flat surface between recesses 26. As illustrated, connecting portion 30 includes a locking device 32 extending upward from first portion 24. Locking device 32 is a flexible member having an engagement lip that engages with a similar locking device provided on second portion 24'. At the distal end of first portion 24, a cut out 34 is provided in each recess 26. Cut out 34 is dimensioned to accommodate distal ends of syringes 14, as discussed herein. In addition, a hinge assembly 36 is provided at the distal end of first portion 24. As illustrated in FIG. 2, hinge assembly 36 comprises a pin 40 having a rod 42 and a head 44 spaced apart from the portion of rod 42 that is attached to first portion 24, and a clamp 48 having a body 50 substantially surrounding a hole 52 located in body 50. Body 50 is illustrated as having an opening to permit insertion of rod 42 of a pin 40 into hole 52, as discussed herein. Clamp 48 is illustrated as having a generally cylindrical shape. In additional embodiments, clamp 48 may have non-cylindrical shapes. In still further embodiments, clamp 48 may not have an opening to permit insertion of rod 42. In other words, body 50 could be solid thereby forming a hole that permits insertion of the head of a pin. The hole should be dimensioned to accommodate the head of the pin, and to permit the rod of the pin to rotate therein. In other embodiments, the pin 40 may be replaced with a spherical structure that doesn't necessarily have a rod portion. The spherical structure is sized to fit in a socket which would replace clamp 48 to permit the spherical structure to rotate in the socket. However, the shape of hole 52 should correspond to the shape of rod 42 of pin 40 so that the two components of hinge assembly 36 engage with each other, as discussed herein. Pin 40 and clamp 48 are located on opposite sides of first portion 24. At the proximal end of first portion 24, a shoulder 54 is provided which is designed to provide a physical gripping portion for a user's hand or fingers. Shoulder 54 is illustrated as also including a lip 55 extending around the perimeter of shoulder 54. Lip 55 is structured and located to help facilitate separation of first portion 24 from second portion 24', or vice versa, for example by pulling the two portions apart. Thus, lip 55 provides a gripping surface to facilitate separation of the two portions of the reusable housing. Shoulder 54 is dimensioned such that it has a height H that is greater than the height of housing 24. In other words, the height H of shoulder 54 permits a portion of the housing to be placed on a flat surface, such as a table or tray, and permits a syringe to be placed in a recess 26 so that the barrel of the syringe does not contact the flat surface to cause the syringe to be raised from housing 24. By reducing the contact between the barrel of the syringe and the flat surface, a relatively secure, fixed engagement can be obtained.

Housing 12 also may include one or more fixed or removable spacers 56 located between the distal end and proximal end of the housing. The spacers are dimensioned to permit the fixed securement of multiple sized syringes or syringes with syringe sleeves. Spacers 56 may be integrally formed as part of housing 24, or may be provided as separate elements that are removable from the housing. The spacers may have various structures to accommodate a number of different types of syringes, for example, one spacer may have a cutout for a 5 mL syringe, and another spacer may have a cutout for a 1 mL syringe. Advantageously, spacers 56 do not hinder the viewing of the contents in the syringes when placed in the housing of the medical apparatus. In addition, spacers advantageously do not cause the syringes or syringe needles attached to the syringes to move along the length of the apparatus when the syringes are placed in the housing.

FIG. 3 provides a perspective view of second portion 24' of housing 12. In this embodiment, second portion 24' is identically structured to first portion 24. Thus, first portion 24 and second portion 24' are structured to matingly engage with each other to define housing 12. In accordance with this embodiment, housing 12 is made by using a single mold to shape first portion 24 and second portion 24'. The portions obtained from the single mold are then fit together to make housing 12. Thus, second portion 24' includes an identical pin and clamp assembly at its distal end so that the pin 42' of second portion 24' mates with clamp 48 of first portion 24, and clamp 48' of second portion 24' mates with pin 42 of first portion 24 when the two portions are assembled together. Locking device 32' similarly engages with locking device 32 to secure first portion 24 and second portion 24' together.

Providing cutouts 34 and 34' in first portion 24 and second portion 24', respectively, permits one of the portions 24 or 24' to rotate over the distal ends of syringes 14. In this embodiment, locking device 32 and 32' can be unlocked to permit housing 12 to be opened to remove one or more of the syringes contained therein. Locking devices 32 and 32' are illustrated as flexible elements having a lip or detent (not shown) spaced away from bridge 30. The detent of each locking device 32 and 32' engages with the other to achieve the desired interlocking relationship. Locking devices 32 and 32' are rigid so that the two locking devices maintain an interlocking relationship, but are flexible to permit a user to flex one of the locking devices away from the other so that they disengage. A magnified view of locking device 32 is illustrated in FIG. 2A. As illustrated, locking device 32 includes a body 32A and a lip 32B extending away from body 32A. To permit the relatively easy disengagement (e.g., disengagement without destroying one or more components of the apparatus) of the locking devices and accordingly, the disengagement of the first and second portions of the housing, the lip includes one or more curved or angled surfaces 32C that permit the lip to more easily disengage from another lip relative to a lip that has straight surfaces or perpendicular surfaces, such as illustrated in FIG. 5, as discussed herein. In one embodiment, surface 32C is at a non-perpendicular angle. In addition, locking device 32 may include a locking surface 32D to engage with lip 32B (not shown) of locking device 32' (see FIG. 3). Similarly, locking device 32' includes a locking surface 32D which engages with lip 32B of locking device 32. Locking surfaces 32D and 32D provide a stronger locking engagement of first portion 24 to second portion 24' than might be provided by the engagement of lips 32B and 32B'. The locking devices may also be disengaged by pulling the first and second portions apart at shoulder 54, as discussed above. Thus, the embodiment of housing 12 illustrated in FIGS. 1–3 can be reusable, if desired.

A housing for a medical injection apparatus in accordance with the invention herein disclosed that is intended for a single use is illustrated in FIGS. 4–7. In other words, the housing of FIGS. 4–7 is structured so that once the housing is assembled to securely hold two or more syringes, the housing cannot be easily reopened to release the syringes. The housing of FIGS. 4–7 is similar to the housing of FIGS. 1–5 where like parts are represented by like numbers increased by 100.

More specifically, FIG. 4 illustrates a housing 112 of a medical injection apparatus. Housing 112 includes a first portion 124 and a second portion (not shown) that are identically structured. First portion 124 is similar to first portion 24 in that it includes a plurality of recesses 126 to accommodate two or more syringes, and to maintain the syringes in a fixed relationship to each other. Recesses 126 are dimensioned to accommodate similarly sized syringes of housing 12. Housing 112 differs from housing 12 in that it is intended to be disposable as compared to being reusable. Thus, housing 112 includes locking devices 132 that are not easy to unlock when first portion 124 is engaged with the second portion of housing 112. More specifically, housing 112 includes one or more locking devices 132 located on an outer edge 125 of first portion 124, and a corresponding number of locking devices 133 on the edge opposite of outer edge 125. In the illustrated embodiment, locking devices 132 are hooks having a body 132A extending from outer edge 125 and a lip 132B extending from the body; and locking devices 133 are holes dimensioned to receive locking devices 132 so that the lips of the hooks engage with an edge of holes 133. Because housing 112 is intended to be disposable, it is not easy to reopen housing 112. The difficulty in reopening the locking devices is due to the sharp angle (e.g., approximately ninety degrees) created between lip 132B and body 132A. Because housing 112 is not structured to be reused, recesses 126 do not necessarily include cut outs similar to housing 12. Housing 112 is assembled by pressing first portion 124 and the second portion together so that locking devices 132 engage with locking devices 133. In addition, housing 112 may include one or more alignment devices (not shown), such as a pin and hole combination, that permit first portion 124 to be aligned with second portion 124'. The alignment devices may be located on bridge 130. In one specific embodiment, at least one alignment device is provided at each of the proximal and distal ends. Furthermore, outer edge 125 is structured to improve the rigidity of housing 112 to reduce undesirable flex of housing 112 during use. Outer edge 125 is also structured, for example by using curved configurations, to reduce catching the edge on other objects, such as gloves worn by the person holding the medical injection apparatus. A similar outer edge may be provided on the embodiment illustrated in FIGS. 1–3. In addition, housing 112 includes one or more fixed or removable inserts or spacers 156 located in recesses 126. In the illustrated embodiment, a spacer 156 is provided at the distal end, and a spacer is provided at the proximal end of first portion 124. Similar spacers are provided in the second portion of housing 112. Spacers 156 are provided to permit different sized syringes to be used within housing 112. More specifically, the medical injection apparatus disclosed herein is structured to accommodate one or more syringe sleeves that are slidable over the needles of the syringes of the medical injection apparatus. The syringe sleeves may be provided as a part of each syringe, or the syringe sleeve may be provided as a component of the medical injection apparatus disclosed herein. When syringe sleeves are used with syringes contained by holder 112, spacers 156 are not required because the syringe sleeves provide the desired fitting relationship of syringes in recess 126. When syringe sleeves are not used, spacers 156 are provided in holder 112 to permit the syringes to be fixedly secured in recesses 126. Similar to the reusable embodiment illustrated in FIGS. 1–3, shoulders 154 have a height H that permits insertion of the syringes into a portion of the housing while the portion is laying flat on a surface, without causing the syringes to substantially contact the surface on which the portion is placed.

FIG. 5 illustrates a bottom plan view of the holder 112 illustrated in FIG. 6. The structural features of locking devices 132 are clearly illustrated. In particular, locking device 132 comprises a body 132A and a lip 132B spaced apart from outer edge 125 of first portion 124. FIG. 6 illustrates a front plan view of holder 112. FIG. 7 illustrates a side plan view of holder 112.

Another housing for a medical injection apparatus in accordance with the invention disclosed herein is illustrated in FIGS. 8–17B. The holder illustrated in FIGS. 8–17B is similar to the holder of FIGS. 1–3, where like parts are identified by like numbers increased by 200. One difference between the holder of FIGS. 8–17B is that the first portion and second portion of the holder are flexibly secured to each other along the width of the holder so that the two portions can be flexibly folded over each other to retain two or more syringes.

More specifically, FIG. 8 illustrates a holder 212 which comprises a first portion 224 and a second portion 224' flexibly attached at a location disposed between the shoulders 254 and 254'. The flexible attachment site of holder 212 defines a hinge assembly 236. Similar to holder 12, holder 212 includes a plurality of recesses 226 structured to receive and retain a plurality of syringes. Each recess 226 is coupled together by a bridge 230. At the proximal ends of first portion 224, a plurality of slots 228 are provided to receive shoulders of the syringes contained therein, and at the proximal end of second portion 224', a similar number of slots 228' are provided. Holder 212 includes a plurality of viewing apertures 222 to permit one to see the contents contained in the syringes. Holder 212 also includes one or more locking devices 232, which are structured to lockingly engage with another locking device, such as locking device 232' to maintain a closed position of holder 212. In addition, a similar locking device 232A is provided near hinge assembly 236 to engage with locking device 232A'.

As illustrated in more detail in FIG. 9, locking device 232A includes a detent 233, and locking device 232A includes a flange 235. Detent 233 is structured and positioned to lockingly engage with flange 235. Hinge assembly 236 is illustrated as a flexible web 237 connecting the two ends of first portion 224 and second portion 224'. In addition, bridge 230 includes a track 231 dimensioned to accommodate a rib of a syringe sleeve, as discussed herein.

FIG. 10 provides a more detailed view of the proximal end of second portion 224', illustrating, among other things, the structural details of locking device 232'. Locking device 232 (FIG. 8) is identically structured to locking device 232'. Housing 212 is illustrated as being structured to be disposable, or in capable of being reused. Thus, as discussed above for housing 112, locking devices 232 and 232' are structured to make it difficult to unlock the locking devices without damaging one or more components of the apparatus. Thus, the lip includes a surface that is oriented at a nearly ninety degree angle to a surface of the body of the locking device. As described for the other embodiments herein, housing 212 includes a shoulder 254 and 254' each having a height that permits insertion of a syringe while one of the two portions is placed on a flat surface.

FIG. 11 illustrates a syringe sleeve 260 that is used with housing 212. Syringe sleeve 260 is illustrated as including a plurality of syringe containers 262 connected to each other by a connecting portion 264. Syringe containers 262 are typically cylindrical structures having an interior bore 272 sized to accommodate a barrel of a syringe. Connecting portion 264 of syringe sleeve 260 includes a rib 268 disposed in a position such that it engages with track 231 of housing 212. Rib 268 is a tapered element with a wider proximal end than the distal end. The asymmetrical structure advantageously provides a unidirectional movement path of syringe sleeve 260 in housing 212. Among other things, this unidirectional movement reduces, and preferably prevents the syringe sleeve from being moved proximally with respect to the housing, and thereby reduces, and preferably prevents, the needles of the syringes from being exposed after administration of a medication to a patient. Connecting portion 264 is illustrated as also including a channel 266 centrally disposed between the syringe containers 262. In additional embodiments, connection portion 264 is solid the entire length of the syringe sleeve so that a channel is not present when locking device 232A is not present and/or is located away from the middle portion of the housing (e.g., located toward the outer edges of the housing). Syringe sleeve 260 also includes a plurality of gripping members 270 which are dimensioned and positioned to extend out of housing 212, when assembled. Gripping members 270 permit a user to grasp syringe sleeve 260 and move the sleeve over the needles. A bottom perspective view of syringe sleeve 260 is illustrated in FIG. 12. Each syringe container 262 also includes an inner ring 274 which is structured to engage with a syringe contained therein. Among other things, inner ring 274 facilitates the desired positioning of the syringe in the syringe sleeve.

FIG. 13 depicts a medical injection apparatus 210 in which housing 212 is partially closed. Medical injection apparatus 210 is illustrated as including a plurality of syringes 14 located in syringe sleeve 260. Syringe sleeve 260 with syringes 14 is placed in first portion 224 of housing 212. Second portion 224' is being closed along arrow A, where the locking devices will engage, as described above, to retain the syringes in the housing. FIG. 14. provides more detail of locking device 232A and 232A', and more specifically, the engagement of detent 233 with flange 235. FIG. 15 provides more detail of locking devices 232 and 232' before they are engaged as second portion 224' is being closed against first portion 224. FIG. 16 provides more detail of rib 268 in track 231. By sliding sleeve (not shown) distally, rib 268 advances distally (i.e., with the narrow end first) and is prevented from moving proximally by the relatively wider proximal end of rib 268.

Figure 17B:
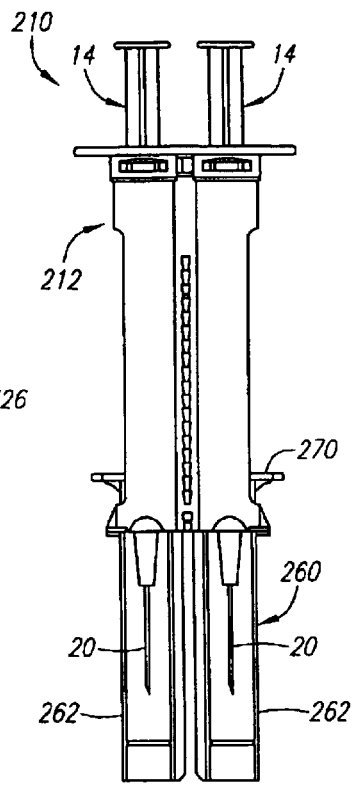
FIG. 17B provides a plan view similar to FIG. 17A with the syringe sleeve in a deployed position, and the hypodermic needles covered.
Figure 21:
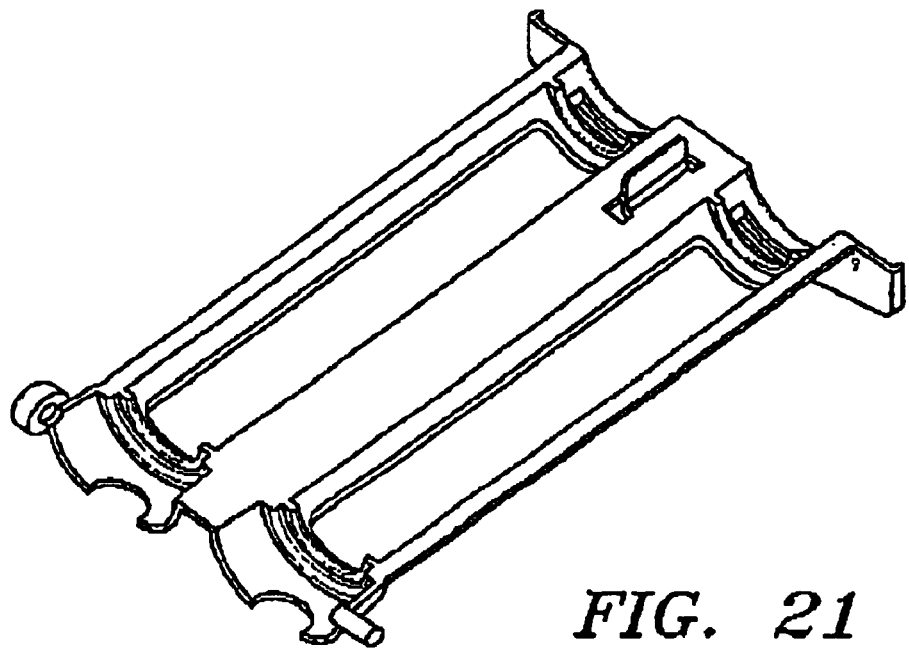
FIG. 21 provides a perspective view of a first portion of a housing similar to FIG. 2 and including a pin and hole hinge assembly.
Figure 22:
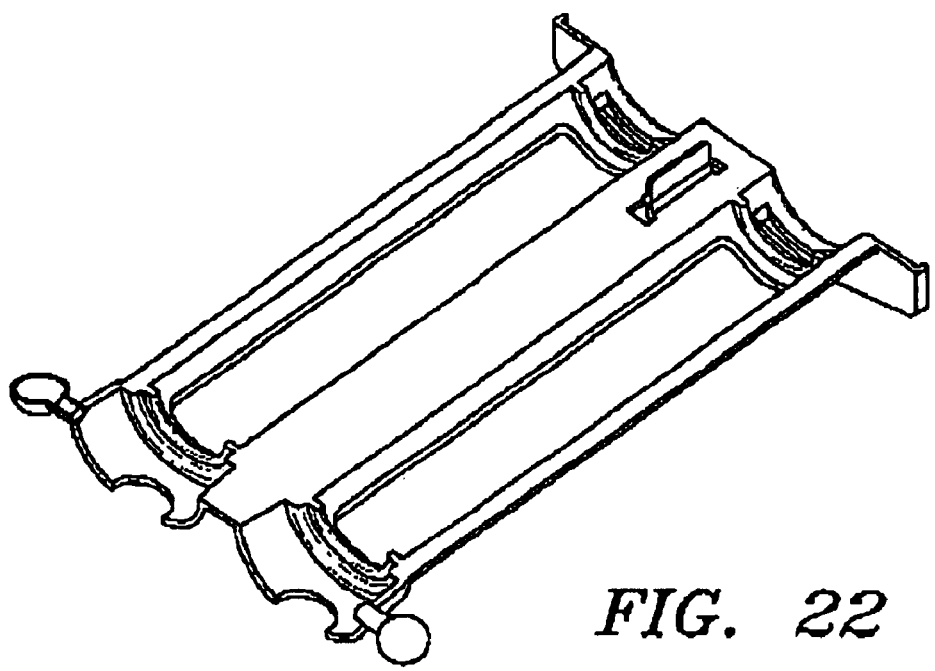
FIG. 22 provides a perspective view of a first portion of a housing similar to FIG. 2 and including a ball and socket hinge assembly.

FIG. 17A depicts a front plan view of medical injection apparatus 210 with two syringes 14 and syringe sleeve 260 held in housing 212. Gripping members 270 of syringe sleeve 260 are illustrated as extending from housing 212. In the position illustrated in FIG. 21A, syringe sleeve 260 is in proximally positioned in housing 212, and the needles of syringes 14 are uncapped. In FIG. 17B, syringe sleeve 260 has been advanced distally to cover needles 20 with syringe containers 262. Due to the unidirectional path of track 231, syringe sleeve 260 cannot be moved proximally, and thus, syringe sleeve 260 is locked in position over needles 20.

Another single-use medical injection apparatus in accordance with the invention herein disclosed is illustrated in FIGS. 18–20B. The medical injection apparatus of FIGS. 18–20B is similar to the medical injection apparatus of FIGS. 1–3, where like parts are identified by like numbers increased by 300.

Figure 19:
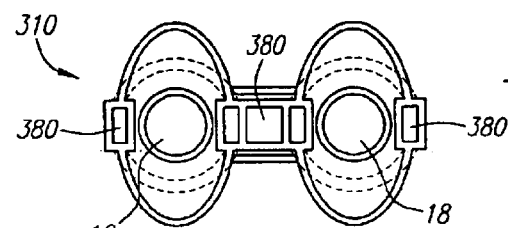
FIG. 19 provides a plan view along line XIX—XIX of FIG. 18.
Figure 20A:
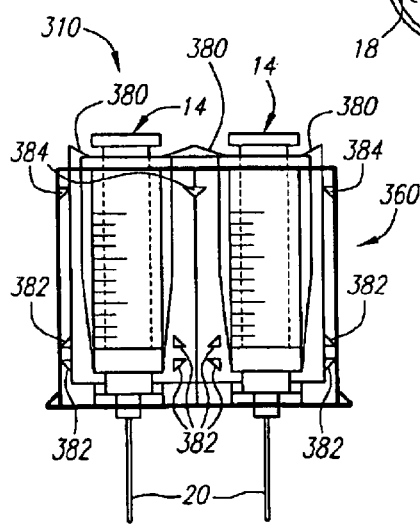
FIG. 20A provides a plan view of the apparatus of FIG. 18 with a safety sleeve in a retracted position, and the hypodermic needles exposed.
Figure 20B:
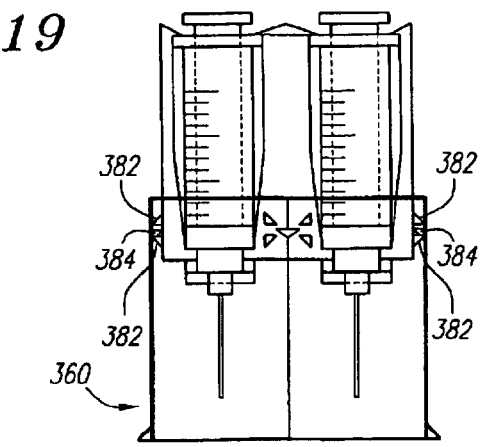
FIG. 20B provides a plan view similar to FIG. 20A with the safety sleeve in a deployed position, and the hypodermic needles covered.

A medical injection apparatus 310 is illustrated as including a housing 312 holding two syringes 14. Housing 312 includes a plurality of recesses 326 for holding syringes 14, and a plurality of locking devices 380 structured to hold syringes 14 in recesses 326. In the illustrated embodiment, locking devices 380 engage with the proximal ends of syringes 14. A top plan view of medical injection apparatus 310 is illustrated in FIG. 19. A sleeve 360 is illustrated disposed over housing 312 in FIG. 20A. Housing 312 illustrated in FIG. 20A includes a plurality of locking devices 382, and sleeve 360 includes a plurality of locking devices 384. Locking devices 382 are located on the outer surface of housing 312, and locking devices 384 are located on the inner surface of sleeve 360. As sleeve 360 is advanced distally to cover needles 20 of syringes 14, as illustrated in FIG. 20B, locking devices 384 engage with locking devices 382 of housing 312. As illustrated, locking devices 382 and 384 are structured to prevent sleeve 360 from being advanced proximally once the locking devices have been engaged. Accordingly, medical injection apparatus 310 is a single-use apparatus.

The medical injection apparatus disclosed herein permits a user to administer two or more medications to a patient at approximately the same time. Preferably, the medications are administered simultaneously, but because the apparatus is configured to operate with conventional syringes, the plungers of the syringes may not be depressed exactly at the same time due to variations if a user's hand anatomy, among other things. Two or more syringes are placed in the recesses of the housing of the medical injection apparatus. The syringes may be preferably pre-filled with a liquid before being placed in the housing, but may be filled after being placed in the housing. For apparatus that include a housing having two portions, as described herein, the portions are placed against each other so that they are lockingly engaged with each other. The portions may be snapped together, or they may be folded over each other along an axis. For apparatus that include a housing without two portions, the syringes may be placed in the recesses, and secured in place within the housing using locking devices provided on the housing. The medications contained in the syringes may then be administered to a patient by inserting the needles into the patient, as is conventionally practiced with conventional syringes. After the needles of the syringes are removed from the patient, a syringe sleeve may be slid distally to cover the needles, and the apparatus may be disposed of. The syringe sleeve may be a unitary structure having a plurality of syringe containers, a unitary structure disposed around the body of the housing, or may be structured to be placed on an individual syringe. The size or number of sleeves should be selected so that all of the needles of the syringes held in the housing are covered after use. When the apparatus employs a reusable housing, the locking devices may be unlocked so that the two portions of the housing are opened. The syringes may then be removed, and discarded.

While this invention has been described with respect to various specific examples and embodiments, for purposes of illustration, it is to be understood that the invention is not limited thereto and that it can be variously practiced within the scope of the following claims.

For example, although the illustrated embodiments of the invention are shown as being structured to hold two syringes, additional embodiments may be structured to hold more than two syringes, so long as the apparatus can be comfortably held in a user's hand. In addition, although the recess of the housing are illustrated as being parallel, other housings may include recesses that are not parallel, but are structured to maintain the desired distance of the distal ends of the needles. In addition, an additional embodiment of the invention includes two or more syringes molded together to define a multi-chambered syringe, and a syringe sleeve slidably disposed over the multi-chambered syringe. This embodiment does not require a separate housing, as described herein, but achieves many of the advantages provided by the invention.

In addition, although the locking devices disclosed herein are illustrated as flexible detents that have a lip that engages with another similarly structured detent, or a flange, other locking devices may be used. Examples of additional locking devices include, and are not limited to pin and hole arrangements, such that the pin includes a portion that can be inserted into a hole, and removed therefrom, and hinged, snap-fitting arrangements, such as a hinge having a recess or hole that engages with a rib provided on the housing after the hinge is passed over the rib.

A number of patents have been referred to herein, each of these patents are hereby incorporated by reference in their entireties.

What is claimed is:

1. A medical injection apparatus for administering two or more medications to a patient, comprising:
a housing having a length and a width, and including at least two recesses along the length of the housing and dimensioned to maintain a corresponding number of syringes in a substantially fixed relationship to each other, each syringe having a hypodermic needle, and a plunger disposed in a barrel of the syringe to direct medication stored in the barrel of the syringe to the hypodermic needle, wherein the housing comprises a first portion and a second portion identically structured to the first portion, each portion structured to matingly engage with the other portion; and a syringe sleeve located around the syringes and being moveable from a first position in which the hypodermic needles of the syringes are exposed for administration of the medication to a second position in which the hypodermic needles are not exposed to prevent inadvertent injury from the needles.

2. The apparatus of claim 1, wherein the housing comprises a hinge assembly defining a pivot axis about which the first portion or the second portion pivots, the axis being parallel to the width of the housing.

3. The apparatus of claim 2, wherein the distal ends of the first portion and the second portion include a cutout dimensioned to accommodate a distal end of each syringe as the first portion or second portion pivots about the pivot axis.

4. The apparatus of claim 2, wherein the hinge assembly is selected from a group consisting of a pin on one side of the housing, and a clamp on an opposite side of the housing; a pin on one side of the housing and a hole on an opposite side of the housing; and a ball on one side of the housing, and a socket on an opposite side of the housing.

5. The apparatus of claim 1, wherein the housing includes at least one locking device located on the first portion and at least one locking device located on the second portion, and positioned to maintain a secure engagement between the fist portion and the second portion.

6. The apparatus of claim 5, wherein the at least one locking device comprises a detent extending from a surface of the first portion.

7. The apparatus of claim 1, wherein the housing includes a first portion having a plurality of hemicylindrical recesses, each recess dimensioned to receive a hypodermic syringe, and a second portion identically structured to the first portion so that the second portion matingly engages with the first portion to form a plurality of cylinders to receive the hypodermic syringes in a substantially fixed relationship.

8. The apparatus of claim 7, wherein the housing includes at least one locking device located on each of the first and second portions, the at least one locking device positioned on the first portion to engage with at least one locking device on the second portion.

9. The apparatus of claim 8, wherein the locking devices of the first portion and the second portion are flexible to permit disengagement of the first portion from the second portion.

10. The apparatus of claim 7, wherein the housing includes a hinge assembly structured to permit the first portion and second portion to pivot about a pivot axis that is parallel to the width of the housing.

11. The apparatus of claim 10, wherein the hinge assembly is selected from a group consisting of a pin disposed on one side of the housing, and a clamp disposed on the opposite side of the housing; a pin on one side of the housing, and a hole on an opposite side of the housing; and a ball on one side of the housing, and a socket on an opposite side of the housing.

12. The apparatus of claim 1, comprising a plurality of syringe sleeves, each syringe sleeve being disposed around each of the syringes.

* * * * *